United States Patent [19]

Cohen

[11] 4,143,428
[45] Mar. 13, 1979

[54] SALINE FILL OF SILICONE PROSTHESIS DURING MAMMAPLASTY AUGMENTATION

[76] Inventor: I. Kelman Cohen, 5104 Cary St. Rd., Richmond, Va. 23226

[21] Appl. No.: 751,215

[22] Filed: Dec. 16, 1976

[51] Int. Cl.² ............................................. A41C 3/10
[52] U.S. Cl. .......................................... 3/36; 128/247
[58] Field of Search ......................... 3/36, 1; 128/247

[56] References Cited

U.S. PATENT DOCUMENTS

| | | | |
|---|---|---|---|
| 3,883,902 | 5/1975 | Lynch ........................................ | 3/36 |
| 3,919,724 | 11/1975 | Sanders et al. ............................ | 3/36 |

*Primary Examiner*—John D. Yasko
*Attorney, Agent, or Firm*—Cushman, Darby & Cushman

[57] ABSTRACT

An assembly for sterile fluid filling of a silicone prosthesis with saline or other fluids from a sterile container having a neck portion screw-threaded in the first sense includes a syringe, a generally tubular connector and a releasable connection between the tubular connector and the syringe. The syringe has a liquid ingress/egress opening at a first end thereof, and the tubular connector completely surrounds this opening and connects the syringe to the container for sterile filling of the syringe with saline from the container. The releasable connection between the tubular connector and the syringe functions so that once the syringe is filled with liquid from the container, the syringe may be detached from the tubular connector while the tubular connector remains in screw-threaded engagement with the container neck. The releasable connection may be a screw-threaded engagement between the tubular connector and the syringe having a second sense, opposite the first sense, of the container neck screw-threaded portion. Alternatively, the releasable connection can comprise a frangible connecting member that fractures when subjected to a shearing action. Augmentation mammaplasty is practiced utilizing the assembly by implanting a silicone prosthesis beneath breast and sequentially filling the syringe with saline of sufficient volume to completely fill the silicone prosthesis, connecting the syringe to the prosthesis, and completely filling the prosthesis with saline from the syringe without detachment of the syringe from connection with the prosthesis.

4 Claims, 4 Drawing Figures

SALINE FILL OF SILICONE PROSTHESIS DURING MAMMAPLASTY AUGMENTATION

BACKGROUND AND SUMMARY OF THE INVENTION

The invention relates to a method for practicing augmentation mammaplasty, and for an assembly particularly adapted for filling of a silicone prosthesis with saline during augmentation mammaplasty. In recent years, the use of implants of silicone filled with saline has become extremely popular, however, the filling of the prosthesis with sterile fluid such as saline is normally a difficult and time-consuming procedure. It is common practice to repeatedly fill a 50 cc syringe until the desired amount of saline has been put into the prosthesis, however, in addition to being time-consuming, this procedure is not fail safe since one can easily miscount and place unequal volumes of saline in each breast prosthesis. Additionally, there can be problems associated with the sterile filling of the syringe with saline since the syringe used in augmentation mammaplasty does not have a needle, but rather merely a nipple providing an ingress/egress opening for liquid.

According to the present invention, a method and an assembly for practicing augmentation mammaplasty are provided that eliminate the problems inherent in the prior art. According to the method of the present invention, augmentation mammaplasty is practiced by implanting a silicone prosthesis beneath a breast and sequentially filling a syringe with saline or other fluid of sufficient volume to completely fill the silicone prosthesis, connecting up the syringe to the prosthesis, and completely filling the prosthesis with saline from the syringe without detachment of the syringe from connection with the prosthesis. The syringe has a volume of 300–400 cc. The step of filling the syringe with saline is accomplished by bringing the first end of a tubular connector releasably connected to the syringe into engagement with the saline bottle neck, filling the syringe with saline by expanding the volume of the syringe and releasing connection between the syringe and the tubular connector. The connection between the syringe and the tubular connector can be provided by screw threads having the opposite sense of screw threads for connecting the first end of the tubular connector to the saline bottle, or by a frangible connecting member, such as a shear-fracturable connecting member.

The assembly according to the present invention for sterile filling of the syringe from a container having a volume approximately larger than or equal to the volume of the syringe and having a neck portion screw-threaded in a first sense, comprises a syringe having a liquid ingress/egress nipple opening at a first end thereof; a generally tubular connecting means completely surrounding the syringe ingress/egress opening and for connecting the syringe to the container, the connecting means having a screw-threaded portion disposed at a first end thereof which screw-threaded portion has said first sense, and providing for connection of the container neck with the tubular connecting means; and releasable means for releasably connecting the tubular connecting means to the syringe so that once filled with liquid from the container, the syringe may be detached from the tubular connecting means while the tubular connecting means remains in screw-threaded engagement with the container. The releasable connecting means may comprise a screw-threaded portion of the tubular connecting means disposed at a second end thereof, opposite said first end, and having a second sense for the screw thread, and screw threads formed on the outside of a portion of the syringe adjacent the ingress/egress nipple opening thereof for cooperating with the second end screw-threaded portion of the tubular connecting means, and having a second sense. Since saline bottles conventionally come with right-hand screw sense, it is preferred that the first end of the tubular connecting means have a right-hand screw sense while the second end thereof (and the syringe) have left-hand screw sense. Alternatively, the releasable means may comprise a frangible connecting member, such as one that is fracturable upon the application of shear forces thereto.

It is the primary object of the present invention to provide an improved method and apparatus for practicing augmentation mammaplasty in particular, and for the sterile filling of syringes in general. This and other objects of the invention will become clear from an inspection of the detailed description of the invention and from the appended claims.

DETAILED DESCRIPTION OF THE INVENTION

Figure 1:
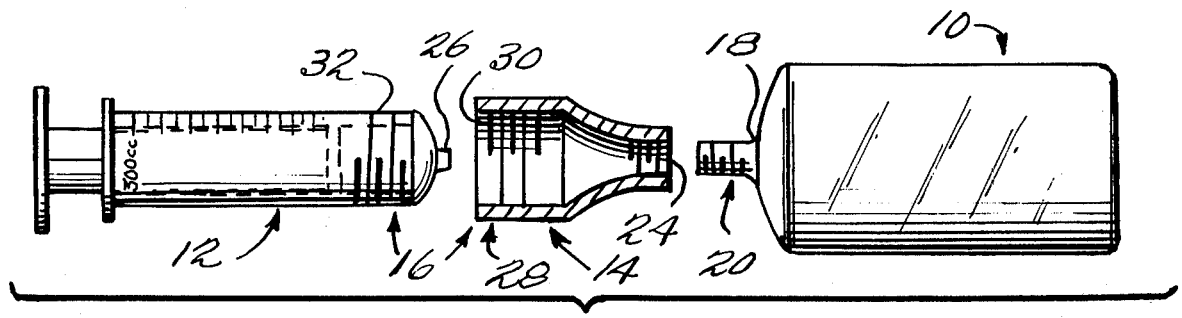
FIG. 1 is a side view, with the connecting means shown in section, of an exemplary assembly according to the invention.
Figure 2:
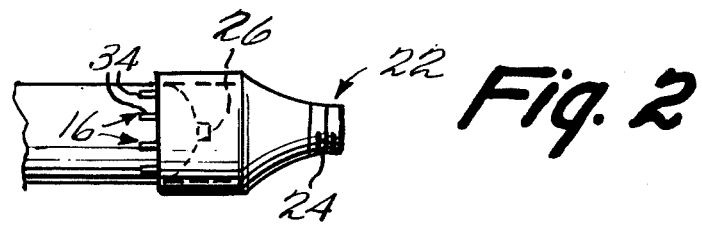
FIG. 2 is a side view of a second embodiment of connector-syringe connecting means.

An assembly according to the present invention is shown in FIG. 1, including a container 10, a syringe 12, a generally tubular connecting means 14, and releasable means 16 for releasably connecting the tubular connecting means 14 to the syringe 12. The syringe has a liquid ingress/egress nipple opening 26 at an end thereof, and the generally tubular connecting means 14 completely surrounds the opening 26 and provides means for connecting the syringe 12 to the container 10 for sterile filling of the syringe with liquid from the container 10. The container 10 has a neck portion 18 thereof that is screw-threaded at 20 in a first sense (i.e., right-hand screws), and the connecting means 14 has a screw-threaded portion 24 disposed at a first end 22 thereof, the screw-threaded portion 24 being screw-threaded in the same sense as the threads 20 (the first sense — i.e., right-hand threads), and provides for connection of the container neck 18 and the tubular connecting means 14. The threaded portion 24 may either be an exteriorly-threaded portion — as shown in FIG. 2 — or an interiorly-threaded portion — as shown in FIG. 1 — depending upon the conventional bottle 10 which it is adapted to cooperate with. Conventional saline bottles some with exteriorly-threaded portions (20) — as shown in FIG. 1 — with screw caps thereon, therefore, the threaded portion 24 of the means 14 will normally be interiorly-threaded.

The generally tubular connecting means 14 need not assume the particular shape shown in the drawings, but may have any shape that provides for connection of a syringe to a container (i.e., a constant cross-section, non-circular cross-sections, etc.). The syringe 12 is shown in the drawings as a piston-type syringe, however, it may be any conventional type of syringe (i.e., a bellows syringe). Preferably, the syringe has a volume of 300-400 cc when the syringe is used for augmentation mammaplasty so that a complete volume for filling the prosthesis during augmentation mammaplasty may be contained by the syringe.

Figure 3:
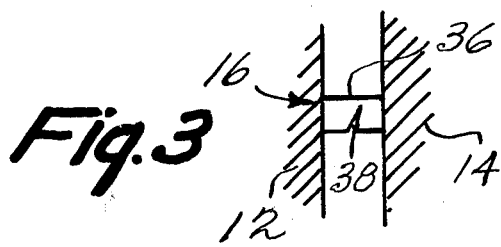
FIG. 3 is a detailed view of a third embodiment of connector-syringe connecting means.

The releasable means 16 may take a variety of forms, as shown in FIGS. 1-3. For instance, as shown in FIG. 1, the tubular connecting means 14 has a second end 28 thereof having screw threads 30 formed thereon, the screw threads 30 cooperating with external screw threads 32 of the same sense on the syringe, the means 30, 32 comprising the releasable means 16. The sense of the screw threads 30, 32 is opposite that of the screw threads 20, 24 so that upon unscrewing of the syringe 12 from the connecting means 14, the connecting means 14 is not unscrewed from the container 10. Since conventional saline containers 10 have necks 18 with right-hand screw-threaded portions 20, it is preferred that the screw-threaded portions 30, 32 have left-hand screw threads.

An alternative form that the releasable means 16 may take is shown in FIGS. 2 and 3, the releasable means 16 in FIGS. 2 and 3 comprising frangible connecting means. The frangible connecting means are shown at 34 in FIG. 2, and comprise fracturable plastic strands that break when a force of predetermined magnitude is exerted on the syringe 12 to move it relative to the connecting means 14. Although the strands 34 may be disposed in the form of a collar completely surrounding the periphery of the members 12 and 14, it is only necessary that a liquid-tight connection be provided between the end of the syringe containing the nipple opening 26 and the connecting means, and any frangible releasing means may be utilized when the liquid-tight connection is provided by the syringe 12 and connecting means 14 themselves (as shown in FIG. 2). As shown in FIG. 3, a shearable connecting piece 36 may be provided, having a shear cut 38 therein, and when relative rotation of the syringe 12 with respect to the tubular connecting means 14 is effected, the member 26 shears along the cut 38.

Figure 4:
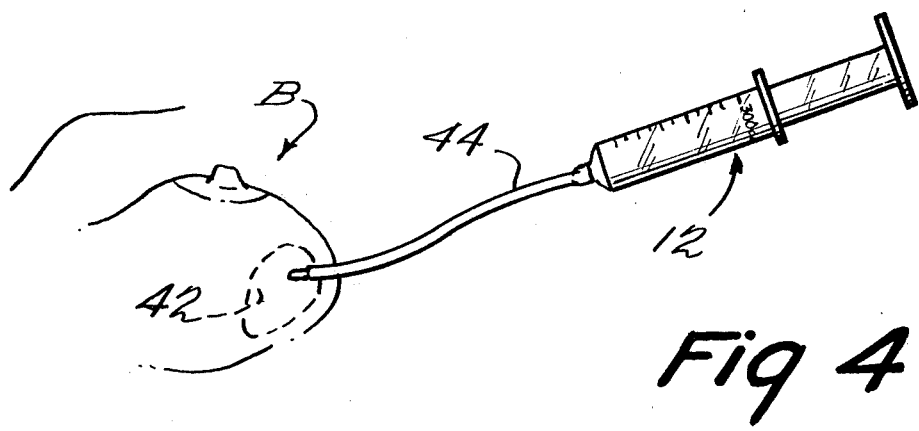
FIG. 4 is a schematic view of the syringe of FIG. 1 during practice of mammaplasty augmentation.

The assembly according to the present invention is most readily adaptable for use according to the method of practicing augmentation mammaplasty according to the invention. The present inventive method of practicing augmentation mammaplasty comprises the steps of implanting a conventional silicone (or other type of inflatable) prosthesis 42 under or on a breast B (see FIG. 4) and then utilizing the assembly according to the invention to fill the prosthesis 42. The silicone prosthesis 42 may be any conventional type, such as those manufactured by McGhan Medical Company of Santa Barbara, California. After implantation of the silicone prosthesis 42, the following sequence of steps is effected: filling a syringe 12 with saline of sufficient volume to completely fill the silicone prosthesis 42; connecting up the syringe 12 to the prosthesis 42; and completely filling the prosthesis 42 with saline from the syringe 12 without detachment of the syringe 12 from connection with the prosthesis 42. Connection between the syringe 12 and prosthesis 42 is conventionally effected by tubing 44 attachable to a portion of the prosthesis and the nipple opening 26 of the syringe 12. The syringe has a volume of 300-400 cc, and the syringe is filled with saline having a volume between 300-400 cc, which volume is sufficient for completely filling the prosthesis 42 without the necessity of constantly detaching and refilling the syringe. This also provides a fail-safe method of insuring that the same amount of saline or other fluid is placed into each prosthesis 42 of each breast B. (For different size prosthesis, 50-500 cc volume syringes may be used.)

The step of filling the syringe with saline is preferably accomplished by bringing the first end 22 of the tubular connector 14 into engagement with the saline bottle neck 18 by clockwise rotation of the connector with respect to the bottle, expanding the volume of the syringe 12 to fill it with 300-400 cc of saline, and then releasing connection between the syringe 12 and the tubular connector 14. The release of connection between the syringe 12 and the tubular connector 14 is accomplished by unscrewing the syringe 12 from the connector 14 by turning the syringe 12 clockwise with respect to the connector (whereby the connection at 20, 24 is maintained), or by breaking of the connectors 34, 36 as by shear-fracturing thereof. Since once the connector 14 is used, it is no longer sterile, it must be discarded; however, if it is desired to fill the same syringe 12 with saline from the same container 10 after one use thereof, another connecting means 14 may be attached to the syringe (as by threads 30, 32) and then to the bottle neck 18, as with the first connecting means 14. While the particular materials of which the various components of the assembly according to the present invention are constructed are not critical, it is preferred that the syringe 12 is of plastic or of glass with a metal collar providing the threads 32, and it is preferred that the connecting means 14 be plastic, as well as the members 34, 36.

It will thus be seen that according to the present invention a method of augmentation mammaplasty has been provided that eliminates many of the drawbacks inherent in the prior art methods, and an assembly for practicing augmentation mammaplasty in particular and for filling a syringe in general has been provided that allows ready, sterile filling of a syringe, the ingress/egress opening of the syringe not being exposed until after filling thereof. Thus, the objects of the present invention have been fulfilled.

While the invention has been herein shown and described as what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies and methods.

What is claimed is:

1. A method of practicing augmentation mammaplasty utilizing a syringe having a generally tubular connector releasably connected thereto, the connector having a first end screw-threaded for engagement with a screw-threaded liquid containing bottle neck, comprising the steps of:

implanting an inflatable prosthesis in a breast, and sequentially sterilly filling the syringe with a sufficient volume of liquid to completely fill the inflatable prosthesis by bringing the first end of the tubular connector into engagement with the liquid containing bottle neck, filling the syringe with liquid by expanding the volume of the syringe, and releasing connection between the syringe and the tubular connector;

connecting up the syringe to the prosthesis; and completely filling the prosthesis with liquid from the syringe without detachment of the syringe from connection with the prosthesis.

2. A method as recited in claim 1 wherein the syringe has a volume of 300–400 cc, wherein said liquid is saline, and wherein said step of filling the syringe with saline is accomplished by filling the syringe with between 300 and 400 cc of saline.

3. A method as recited in claim 1 wherein the first end of the connector is connected to the bottle by clockwise rotation of the connector with respect to the bottle, and wherein said step of releasing connection between the connector and the syringe is accomplished by unscrewing the syringe from the connector by turning the syringe clockwise with respect to the connector.

4. A method as recited in claim 1 wherein said step of releasing connection between the connector and the syringe is accomplished by shear-fracturing a connection between the connector and the syringe.

* * * * *